United States Patent [19]

Nudelman et al.

[11] 4,229,574

[45] Oct. 21, 1980

[54] INDOLE CEPHALOSPORIN DERIVATIVES

[75] Inventors: Abraham Nudelman, Rehovot; Abraham Patchornik, Ness-Ziyona, both of Israel

[73] Assignee: Yeda Research and Development Co., Ltd., Rehovot, Israel

[21] Appl. No.: 68,888

[22] Filed: Aug. 23, 1979

Related U.S. Application Data

[62] Division of Ser. No. 947,541, Oct. 2, 1978, which is a division of Ser. No. 858,630, Dec. 8, 1977, Pat. No. 4,139,703.

[51] Int. Cl.² ............................................ C07D 501/56
[52] U.S. Cl. ............................................ 544/21; 544/22
[58] Field of Search ............................... 544/21, 22

[56] References Cited

U.S. PATENT DOCUMENTS 4,000,133  12/1976  Kariyone et al. .................. 424/246

*Primary Examiner*—Paul M. Coughlan, Jr.
*Attorney, Agent, or Firm*—William J. Stein; L. Ruth Hattan; George W. Rauchfuss, Jr.

[57] ABSTRACT

New indole derivatives of cephalosporin compounds have been prepared which are useful as antibiotics.

5 Claims, No Drawings

INDOLE CEPHALOSPORIN DERIVATIVES

This is a division of application Ser. No. 947,541, filed Oct. 2, 1978, which is a division of application Ser. No. 858,630 filed Dec. 8, 1977, which issued on Feb. 13, 1979, as U.S. Pat. No. 4,139,703.

BACKGROUND OF THE INVENTION

This invention is directed to new and useful cephalosporin derivatives and methods of preparing said derivatives.

SUMMARY OF THE INVENTION

Compounds of Formula 1

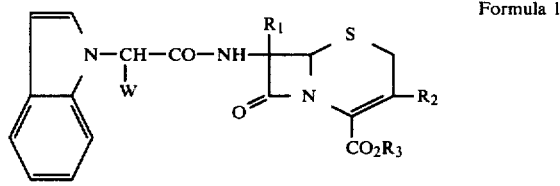

Formula 1 are useful as antibiotics wherein W is hydrogen or a $CO_2R_4$ group wherein $R_4$ is hydrogen, a straight or branched 1 to 4 carbon alkyl group, a straight or branched alkanoyloxymethyl group in which the alkanoyl group has from 2 to 5 carbon atoms; $R_1$ is hydrogen or methoxy; $R_2$ is methyl, chloro, bromo, methoxy, acetyloxymethyl, 1,3,4-thiadiazol-2-ylthiomethyl, 5-methyl-1,3,4-thiadiazol-2-ylthiomethyl, tetrazol-5-ylthiomethyl, 1-methyltetrazol-5-ylthiomethyl, 1,3,4-oxadiazol-2-ylthiomethyl, 5-methyl-1,3,4-oxadiazol-2-ylthiomethyl, 1-methyl-1,2,3-triazol-5-ylthiomethyl, 1,2,3-triazol-5-ylthiomethyl, $R_3$ is hydrogen, a straight or branched alkyl group of from 1 to 4 carbon atoms, a straight or branched alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched alkyl group having 1 to 4 carbon atoms; and alkoxycarbonylaminomethyl group in which the alkoxy moiety is straight or branched and has from 1 to 4 carbon atoms and the amine nitrogen may be substituted with a straight or branched alkyl group of from 1 to 4 carbon atoms, p-(alkanoyloxy)benzyl group in which the alkanoyl moiety is straight or branched and has from 2 to 5 carbon atoms; an aminoalkanoyloxymethyl group in which the alkanoyl moiety has from 2 to 15 carbon atoms and the amino nitrogen may be mono- or di-substituted with a straight or branched alkyl group having from 1 to 4 carbon atoms; or pharmaceutically acceptable salts thereof.

DETAILED DESCRIPTION OF THE INVENTION

In Formula 1 the substituent group as represented by $R_3$ in addition to being hydrogen may also be alkanoyloxymethyl as represented by the structure

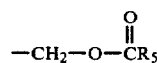

wherein $R_5$ is selected from a straight or branched alkyl group of from 1 to 4 carbon atoms; $R_3$ is an alkanoylaminomethyl or alkoxycarbonylaminomethyl as represented by the structure

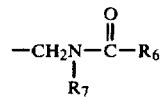

Wherein $R_6$ represents a straight or branched alkyl group of from 1 to 4 carbon atoms or a straight or branched alkoxy group of from 1 to 4 carbon atoms, and $R_7$ is selected from hydrogen and a straight or branched alkyl group of from 1 to 4 carbon atoms; $R_3$ is a p-(alkanoyloxy)benzyl as represented by the structure

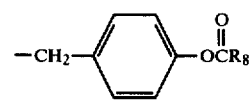

wherein $R_8$ is a straight or branched alkyl group of from 1 to 4 carbon atoms; and $R_3$ is aminoalkanoyloxymethyl as represented by the group

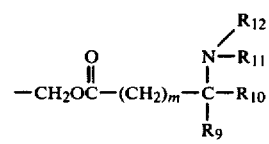

wherein m is 0 to 5, each of $R_9$ and $R_{10}$ is selected from hydrogen or a straight or branched alkyl group of from 1 to 4 carbon atoms, and each of $R_{11}$ and $R_{12}$ is selected from hydrogen or a straight or branched alkyl group of from 1 to 4 carbon atoms.

Illustrative examples of straight or branched alkyl groups of from 1 to 4 carbon atoms which $R_5$ to $R_{12}$ inclusive may represent are methyl, ethyl, n-propyl, iso-propyl, n-butyl, sec-butyl and tert-butyl. $R_6$ may represent a methoxy, an ethoxy, a propoxy or a tert-butoxy group.

In Formula 1, the substituent group $R_2$ may represent in addition to methyl, acetyloxymethyl, chloro, bromo or methoxy, a heterocyclic thio group selected from 1,3,4-thiadiazol-2-ylthiomethyl, 5-methyl-1,3,4-thiadiazol-2-ylthiomethyl, tetrazol-5-ylthiomethyl, 1-methyltetrazol-5-ylthiomethyl, 1,3,4-oxadiazol-2-ylthiomethyl, 5-methyl-1,3,4-oxadiazol-2-ylthiomethyl, 1,2,3-triazol-5-ylthiomethyl, or 1-methyl-1,2,3-triazol-5-ylthiomethyl, as represented by the following respective structures:

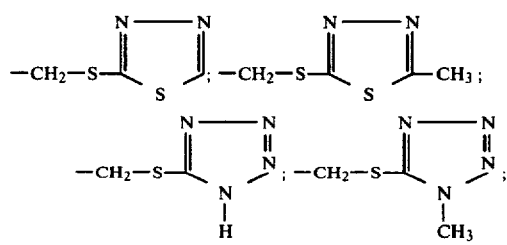

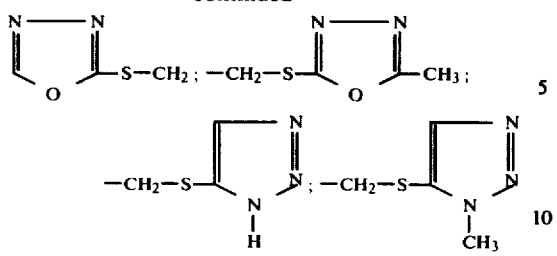

In Formula 1, $R_1$ is hydrogen or methoxy. It is apparent that the group $R_1$ may be either cis or trans to the hydrogen atom at the 6-position of the cephalosporin derivative. Those compounds in which the $R_1$ group is cis to the 6-position hydrogen are preferred.

In Formula 1, W may represent hydrogen, a —$CO_2R_4$ group in which $R_4$ is hydrogen, a straight or branched alkyl group of 1 to 4 carbon atoms or an alkanoyloxymethyl group in which the alkanoyl group is straight or branched and has from 2 to 5 carbon atoms.

The non-toxic pharmaceutically acceptable inorganic acid addition salts of compounds of this invention such as mineral acid addition salts, for example, hydrogen chloride, hydrogen bromide, hydrogen iodide, sulfates, sulfamate, phosphate, and organic acid addition salts, for example, maleate, acetate, citrate, oxalate, succinate, benzoate, tartrate, fumarate, malate, mandelate, and ascorbate, are also included within the scope of this invention.

Also within the scope of this invention are the non-toxic pharmaceutically acceptable salts of the compounds of Formula 1 of this invention wherein W represents —$CO_2R_4$ ($R_4$=H), and the compounds wherein $R_3$ represents hydrogen. Illustrative non-toxic pharmaceutically acceptable salts of these acid derivatives include the alkali metal and alkaline earth metal salts such as the sodium, potassium, calcium or magnesium salts and the primary, secondary, or tertiary amine salts, for example, cyclohexylamine, diethylamine, and pyridine.

The compounds of this invention may be administered in a manner similar to that of many well-known cephalosporin compounds, for example, cephalexin, cephalothin, or cephaloglycine. They may be administered alone or in the form of pharmaceutical preparations etiher orally or parenterally and topiclly to warm blooded animals, that is, birds, and mammals, for example, cats, dogs, cows, sheep and horses, and humans. For oral administration, the compounds may be administered in the form of tablets, capsules or pills or in the form of elixirs or suspensions. For parenteral administration, they may be used in the form of a sterile aqueous solution which may contain other solutes, for example, enough saline or glucose to make the solution isotonic. For topical administration, the compounds may be incorporated in creams or ointments.

Illustrative examples of bacteria against which the compounds of this invention are active are Staphylococcus aureus, Salmonella schottmulleri, Klebsiella pneumoniae, Diplococcus pneumoniae, and Streptococcus pyogenes.

An illustrative example of a cephalosporin derivative of this invention is 7-[[(1H-indol-1-yl)acetyl]amino]-3-[[(1-methyl-1H-tetrazol-5-yl)thio]methyl]-8-oxo-5-thia-1-azabicyclo[4.2.0]oct-2-ene-2-carboxylic acid.

The compounds of this invention as represented by Formula 1 are prepared by coupling compounds of Formula 2

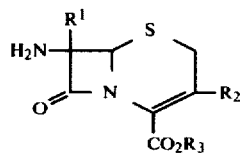

Formula 2 wherein $R_1$, $R_2$ and $R_3$ has meanings defined for Formula 1 with compounds of Formula 3

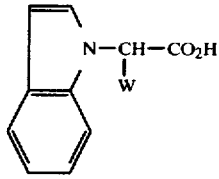

Formula 3 wherein W has the meaning defined for Formula 1 and functional equivalents thereof. Optionally, the compounds of this invention may also be prepared by couplig a compound of Formula 2 with a compound of Formula 3 either in the presence of N-ethoxy-2-ethoxy-1,2-dihydroquinoline provided $R_3$ and $R_4$ are other than hydrogen or in the presence of a dehydrating agent such as a carbodiimide.

Functional equivalents of the acids as represented by Formula 3 include the acid halide, for example, the acid chloride, acid anhydrides, including mixed anhydrides with for example alkylphosphoric acid, lower aliphatic monoesters of cabonic acid or alkyl or aryl sulfonic acids.

The coupling reaction is generally carried out in the presence of a solvent. Suitable solvents include ethyl acetate, acetone, dioxane, acetonitrile, chloroform, ethylene chloride, tetrahydrofuran, dimethylformamide, ether, ethanol, ethanol-benzene and benzene. As hydrophilic solvents are employed, mixtures of these solvents with water are also suitable for the above reactions. The coupling reaction is generally carried out in the presence of a base, for example, triethylamine or an alkaline bicarbonate. The temperature of the reaction may vary from −10° to 100° C., and the reaction time may vary from about ½ hour to 10 hours. The cephalosporin products are isolated by conventional methods.

Illustrative examples of coupling reactions useful in obtaining compounds of Formula 1 are as follows.

The general method described by Spencer, et al., J. Med. Chem., 9, 746 (1966) is used to form Formula 1 compounds. An acid of Formula 3 is first converted to a functional equivalent (mixed anhydride) by reacting the acid with an alkylchloroformate in the presence of an acid acceptor (for example, triethylamine) in a solvent at about −10° C. The amine with which the acid is to be coupled to form compounds as represented by Formula 1 is added and the temperatures increased from about −10° C. to about room temperature (about 20° C.). The reaction is completed and the coupled product is recovered by conventional methods. If the acid of Formula 3 contains a —$CO_2R_4$ group, then $R_4$ is other than hydrogen or a cation.

Another illustrative method used to prepare compounds of Formula 1 involves the coupling of 1 equivalent of an acid as represented by compounds of Formula 3 with 1 equivalent of an amine as represented by compounds of Formula 2 in the presence of about 1 to 2 equivalents of a carbodiimide in a solvent such as tetrahydrofuran optionally containing a base such as triethylamine at a temperature from about −5° C. to about 30° C. according to the general procedure described in U.S. Pat. No. 3,252,973. $R_1$, $R_2$, $R_3$ and W are as defined for Formula 1.

Optionally, acids as represented by compounds of Formula 3 may be coupled with compounds as represented by Formula 2 in the presence of N-ethoxycarbonyl-2-ethoxy-1,2-dihydroquinoline (EEDQ) provided that $R_3$ and $R_4$ are other than hydrogen or a cation. Using the general method of Belleau, et al., *J. Am. Chem. Soc.*, 90, 1651 (1968), equivalent amounts of the acid, the amine and EEDQ are stirred in a suitable solvent for 2 to 12 hours at a temperature of about 20° C. to about 70° C. The coupled product is recovered by conventional techniques.

Illustratively, a compound as represented by Formula 3 wherein W is —$CO_2R_4$ and $R_4$ is hydrogen is coupled to compounds as represented by Formula 2 using the general procedure as described in U.S. Pat. No. 3,282,926. The monoacid chloride of a compound of Formula 3 is prepared by reacting one equivalent of the acid with 1 equivalent of thionyl chloride in ether at from 0° to about 30° C. for from 0.5 to 2 hours, removing the ether and excess thionyl chloride and reacting the monoacid chloride with the 7-amino derivative of a compound of Formula 2 in the presence of an acid acceptor at a temperature of about 0° C. to about 30° C. for from 30 minutes to 2 hours to give the coupled compound which is recovered by conventional techniques.

Compounds of Formula 2 wherein $R_1$ is hydrogen, $R_3$ is hydrogen, or a cation and $R_2$ is methyl or acetyloxymethyl are commercially available or may be prepared by the methods well-known in the art. The corresponding compounds wherein $R_1$ is methoxy, $R_2$ is methyl or acetyloxymethyl and $R_3$ is hydrogen may be prepared by the general procedures described in U.S. Pat. No. 3,778,432.

Compounds of Formula 2 wherein $R_2$ is chloro, bromo or methoxy may be prepared as described by the general procedure in *J. Am. Chem. Soc.*, 96, 4986 (1974) and *J. Med. Chem.*, 18, 403 (1975) wherein $R_1$ is hydrogen or methoxy and $R_3$ is hydrogen.

Compounds of Formula 1 and 2 wherein $R_3$ is alkanoyloxymethyl may be prepared by reacting the corresponding acid, $R_3$ is hydrogen, in the form of a salt, such as, an alkali metal salt or the triethylammonium salt with a compound of the formula:

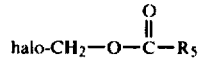

wherein halo is chlorine or bromine, and $R_5$ is a straight or branched alkyl group of from 1 to 4 carbon atoms, by the general procedure described in U.S. Pat. No. 3,655,658.

Compounds of Formulas 1 and 2 wherein $R_3$ is alkanoylaminomethyl or alkoxycarbonylaminomethyl are prepared by treating the sodium salt of the corresponding acid ($R_3$=hydrogen) derivatives of Formulas 1 and 2 in an organic solvent such as dimethylformamide or hexamethylphosphoramide at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of Formulas 1 and 2 wherein $R_3$ is p-(alkanoyloxy)benzyl are prepared by adding two equivalents of the p-(alkanoyloxy)benzyl alcohol to a suspension of the sodium salt of the corresponding acid derivative, $R_3$=hydrogen, of Formulas 1 and 2 and dimethylformamide or hexamethylphosphoramide after which the mixture is cooled to 0° C. 1.2 equivalents of dicyclohexylcabodiimide and dimethylformamide are added dropwise to the mixture with stirring. The mixture is stirred at 0° C. for ½ to 3 hours and then an additional 2 to 5 hours at room temperature. The formed dicyclohexylurea is removed by filtration. The filtrate is diluted with chloroform, methylene chloride or ethylacetate, washed with water, dried and evaporated to give the product.

Compounds of Formulas 1 and 2 wherein $R_3$ is aminoalkanoyloxymethyl are prepared by mixing a suspension of the sodium salt of the corresponding acid, $R_3$=hydrogen, of Formulas 1 and 2 and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride washed with water, aqueous base, then water. The organic phase is separated and the precipitate isolated by conventional means followed by deprotection of the amine group to give the product.

Compounds represented by Formula 1 and 2 wherein $R_1$ is hydrogen or methoxy, $R_2$ is a heterocyclic thiomethyl group as described in Formula 1 and $R_3$ is hydrogen are prepared by dissolveing 1 equivalent of an acid, represented by compounds of Formula 1 or 2 wherein $R_1$ is hydrogen or methoxy, $R_2$ is acetyloxymethyl, and $R_3$ is hydrogen, in the form of a salt, such as the sodium salt, in about 500 to 2000 ml of water at a temperature of from about 30° to about 90° C. under a nitrogen atmosphere, and then adding 1 equivalent of a base, such as, sodium bicarbonate or triethylamine and 1 to 3 equivalents of the appropriate heterocyclic thiol selected from a compound having the following structure:

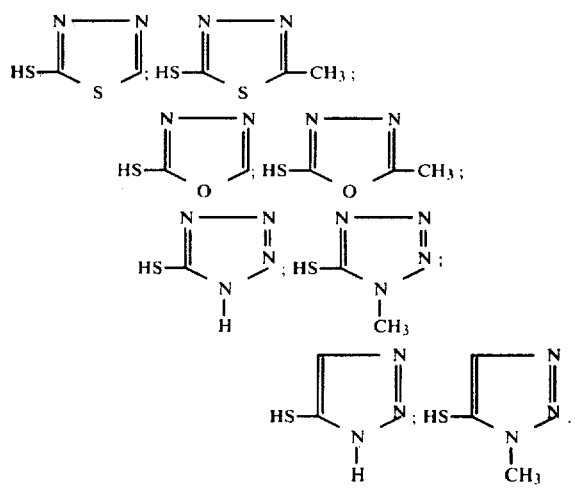

The displacement of the acetyloxy group by the heterocyclic thiol compounds is also realized when compounds of Formula 1, $R_1$ is hydrogen or methoxy, $R_2$ is acetyloxymethyl, and $R_3$ is hydrogen, are treated with an appropriate heterocyclic thiol according to the general procedure described in *J. Antibiotics*, 23, 131 (1966).

Compounds of Formula 3 wherein W is hydrogen are commercially available. Alternatively compounds of Formula 3 wherein W is hydrogen, or COOH are prepared by a modification of the general procedure described by Barco, et al., *Synthesis*, 124 (1976). An appropriate alkyl 2-bromo- or 2-chloro-acetate such as ethyl 2-bromoacetate or an alkyl 2-bromo- or 2-chloromalonate such as diethyl 2-bromomalonate is reacted with an equimolar amount of indole in a mixture of water-benzene in the presence of sodium hydroxide and tetraalkylammonium salt. The mixture is stirred at 10° to 100° C. until no more indole is detected by thin layer chromatography. Upon acidification and removal of the solvents the desired compounds of Formula 3 are obtained. The half-esters of compounds of Formula 3 are prepared by methods well known in the art.

Optionally, compounds of Formula 1 wherein $R_3$ and $R_4$ are both hydrogen can be prepared by subjecting compounds of Formula 1 wherein either one of or both of $R_3$ and $R_4$ is other than hydrogen or a cation to trifluoroacetic acid at about 0° C. for about 10 minutes to 1 hour so as to hydrolyze a group from the carboxyl group to form the free acid. The general procedure described in U.S. Pat. No. 3,657,232 is employed.

The preferred compounds of this invention are those compounds of Formula 1, wherein W is hydrogen, —$CO_2R_4$, wherein $R_4$ is hydrogen or an alkyl group, $R_1$ is hydrogen, $R_2$ is acetyloxymethyl or a heterocyclic thiomethyl group and $R_3$ is hydrogen.

It has been observed that 7-[[(1H-indol-1-yl)acetyl)]-amino]-3-[[(1-methyl-1H-tetrazol-5-yl)thio)methyl]-3-oxo-5-thia-1-azabicyclo[4.2.0]oct-2-ene-2-carboxylic acid shows in vivo oral activity at a concentration of 14.9 mg/Kg/dose against streptococcus pyogenes ST 139. This oral activity is unusual and unexpected for substituted acetamido cephalosporins which leak an α-amino group.

The daily dosage of the active ingredient may range from 1 mg to about 500 mg. The exact amount will vary with the patients size, age and type of infection.

A typical tablet can have the following composition:

| | |
|---|---|
| 7-[(1H-indol-1-ylacetyl)amino]-3-[[(1-methyl-1H-tetrazol-5-yl)thio]methyl]-3-oxo-5-thia-1-azabicyclo[4.2.0]oct-2-ene-2-carboxylic acid | 50 mg |
| Lactose, USP | 250 mg |
| Corn Starch, USP | 50 mg |
| Corn Starch, USP (as 10% starch paste) | 5 mg |
| Calcium Stearate | 2 mg |

Suitable size tablets can be prepared using a 5/16 inch diameter standard concave punch.

A typical ointment can have the following composition: 7-[(1H-indol-1-ylacetyl)amino]-3-[[(1-methyl-1H-tetrazol-5-yl)thio]methyl]-8-oxo-5-thia-1-azabicyclo[4.2.0]oct-2-ene-2-carboxylic acid, 50 mg/grams of ointment.

| Hydrophilic Base | |
|---|---|
| Cetyl alcohol | 15% |
| White Wax | 1% |
| Sodium Lauryl sulfate | 2% |
| Propylene glycol | 10% |
| Water | 72% |

Add the cephalosporin derivative to a small amount of water and incorporate into the base.

A typical parenteral solution may have the following composition:

| | |
|---|---|
| 7-[(1H-indol-1-ylacetyl)amino][[(1-methyl-1H-tetrazol-5-yl)thio]methyl]-8-oxo-5-thia-1-azabicyclo[4.2.0]oct-2-ene-2-carboxylic acid | 1.0 g |
| White beeswax | 1.0 g |
| Peanut oil, to make | 10.0 cc |

Melt wax into a portion of the peanut oil and then add the remaining oil to the mix. Sterilize the mix at 150° C. for 2 hours with dry heat. Under sterile conditions mix the cephalosporin into the wax-oil mixture and place in an ampule and seal said ampule. For use, dilute contents of ampule with 10 cc of pure water. Each cc contains 50 mg of cephalosporin.

EXAMPLE 1

(1H-Indol-1-yl)acetic Acid

To a solution of ethyl 2-bromoacetate (25 g, 0.15 mole) and indole (11.7 g, 0.1 mole) in 100 ml of benzene is added a solution of sodium hydroxide (25 g, 0.626 mole) in 50 ml of water. To the obtained mixture is added tetra-n-butylammonium bromide (1.6 g, 0.5 mmole). The mixture is stirred at 25° C. for 16 hours. The aqueous phase is acidified to pH 3. The organic phase is separated, dried and evaporated to give the title compound in 92% yield. NMR (DMSO-$D_6$) ppm (δ) 5.05 (s, 2); 6.50 (d, 1), 6.9–7.8 (m, 5).

EXAMPLE 2

(1H-Indol-1-yl)malonic Acid

To a solution of diethyl 2-bromomalonate (0.15 m) and indole (0.1 m) in 100 ml of benzene is added a solution of sodium hydroxide (0.1 m) in water. To this mixture is added tetra-n-butylammonium bromide (0.5 mmole). This mixture is stirred at about 25° C. for 16 hours. The phases are separated, the organic phase is dried and evaporated to give diethyl (1H-indol-1-yl)malonate.

To a solution of diethyl (1H-indol-1-yl)malonate (0.02 mole) in 25 ml of absolute ethanol is added 25 ml (0.02 mole) of 0.8 N ethanolic potassium hydroxide. This solution is stirred overnight. The solvent is flash evaporated and the residue is dissolved in 25 ml of water and washed twice with 50 ml of ether. The aqueous phase is separated, acidified to pH of 2.5, saturated with sodium chloride and extracted twice with 80 ml of ether. The ether extracts are combined, dried and evaporated to give the monoethyl ester of (1H-indol-1-yl)malonic acid.

A solution of (0.02 mole) of the diethyl ester of (1H-indol-1-yl)malonic acid in 25 ml of absolute ethanol is mixed with 50 ml of 0.8 N alcoholic potassium hydroxide (0.04 mole) and stirred overnight at room temperature. The solution is evaporated to dryness.

The residue is dissolved in a small amount of water and acidified to pH of 2 with 6 N hydrochloric acid. The aqueous phase is extracted with ether. The ether extracts are combined, dried and evaporated to give (1H-indol-1-yl)malonic acid.

EXAMPLE 3

7-[[(1H-Indol-1-yl)acetyl]amino]-3-[[(1-methyl-1H-tetrazol-5-yl)thio]methyl]-8-oxo-5-thia-1-azabicyclo[4.2.0]oct-2-ene-2-carboxylic acid A solution of (1H-indol-1-yl)acetic acid (3.5 g, 0.02 mole) and triethylamine (2.48 ml, 0.02 mole) in 80 ml of tetrahydrofuran is cooled to 0° C. While stirring, isobutyl chloroformate (2.6 ml, 0.02 mole) is added and the temperature maintained at 0° C. for 15 min. A cold solution of 3-[[(1-methyl-1H-tetrazol-5-yl)thio]methyl]-7-amino-8-oxo-5-thia-1-azabicyclo[4.2.0]oct-2-ene-2-carboxylic acid (6.56 g, 0.02 mole) and triethylamine (2.48 ml, 0.02 mole) in 72 ml of 50% aqueous tetrahydrofuran is added with stirring to the previous solution.

The mixture is stirred at 5° C. for 1 hour and at room temperature for an additional hour. The tetrahydrofuran is evaporated and the residue is dissolved in 100 ml of water and is washed with ethyl acetate. The aqueous phase is covered with a fresh layer of ethyl acetate, cooled in ice and acidified to pH 3 with 6 N hydrochloric acid. The mixture is filtered and the ethyl acetate separated. The aqueous phase is washed with fresh ethyl acetate. The combined ethyl acetate fractions are dried over magnesium sulfate, treated with charcoal, filtered, flash concentrated to 10–30 ml and added with vigorous stirring to a mixture of ether-hexane. The title compound is recovered as a solid in 25% yield.

NMR (DMSO−$D_6$+$D_2O$) ppm ($\beta$) 3.75 (broad s, 2), 3.98 (s, 3), 4.32 (broad s, 2), 5.0 (s, 2), 5.1 (d, 1), 5.72 (d, 1), 6.5 (d, 1), 6.9–7.7 (m, 5).

In like manner and using equivalent amounts of 3-[[(1-methyl-1H-tetrazol-5-yl)thio]methyl]-7-amino-7-methoxy-8-oxo-5-thia-1-azabicyclo[4.2.0]oct-2-ene-2-carboxylic acid in place of 3-[[(1-methyl-1H-tetrazol-5-yl)thio]methyl]-7-amino-8-oxo-5-thia-1-azabicyclo[4.2.0]oct-2-ene-2-carboxylic acid gives 7-[[(1H-indol-1-yl)acetyl]amino]-7-methoxy-3-[[(1-methyl-1H-tetrazol-5-yl)thio]methyl]-8-oxo-5-thia-1-azabicyclo[4.2.0]oct-2-ene-2-carboxylic acid.

EXAMPLE 4

7-[[(H-Indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid The title compound is obtained in 21% yield by the procedure as described in Example 3 when 3-[[(5-methyl-1,3,4-thiadiazol-2-yl)thio]methyl]-7-amino-8-oxo-5-thia-1-azabicyclo[4.2.0]oct-2-ene-2-carboxylic acid is used instead of 3-[[(1-methyl-1H-tetrazol-5-yl)thio]methyl]-7-amino-8-oxo-5-thia-1-azabicyclo[4.2.0]oct-2-ene-2-carboxylic acid.

NMR (DMSO-$D_6$) 2.67 (s, 3), 3.7 (broad s, 2), 4.3 (broad s, 2), 4.98 (s, 2), 5.1 (d, 1), 5.7 (m, 1), 6.5 (m, 1), 6.9–7.7 (m, 5).

In like manner and using equivalent amounts of monoethyl ester of 1H-indol-1-ylmalonic acid in place of 1H-indol-1-ylacetic acid gives 7-[[2-carbethoxy-2-(1H-indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid.

EXAMPLE 5

7-[[(1H-Indol-1-yl)acetyl]amino]-3-methyl-8-oxo-5-thia-1-azabicyclo[4.2.0]oct-2-ene-2-carboxylic acid The title compound is obtained in 58% yield by the procedure as described in Example 3 when 7-amino-3-methyl-8-oxo-5-thia-1-azabicyclo[4.2.0]oct-2-ene-2-carboxylic acid is used instead of 3-[[(1-methyl-1H-tetrazol-5-yl)thio]methyl]-7-amino-8-oxo-5-thia-1-azabicyclo[4.2.0]oct-2-ene-2-carboxylic acid.

NMR (DMSO-$D_6$) 2.07 (s, 3), 3.5 (broad s, 2), 5.01 (s, 2), 5.1 (d, 1), 5.67 (q, 1), 6.5 (d, 1). 6.9–7.7 (m, 5).

EXAMPLE 6

3-[(Acetyloxy)methyl]-7-[[(1H-indol-1-yl)acetyl]amino]-8-oxo-5-thia-1-azabicyclo[4.2.0]oct-2-ene-2-carboxylic acid The title compound is obtained by the procedure as described in Example 3 when 3-[(acetyloxy)methyl]-7-amino-8-oxo-5-thia-1-azabicyclo[4.2.0]oct-2-ene-2-carboxylic acid is used instead of 3-[[(1-methyl-1H-tetrazol-5-yl)thio]methyl]-7-amino-8-oxo-5-thia-1-azabicyclo[4.2.0]oct-2-ene-2-carboxylic acid.

EXAMPLE 7

7-[[(1H-Indol-1-yl)acetyl]amino]-3-[[(1-methyl-1H-tetrazol-5-yl)thio]methyl]-8-oxo-5-thia-1-azabicyclo[4.2.0]oct-2-ene-2-carboxylic acid 3-[(Acetyloxy)methyl]-7-[[2-1H-indol-1-ylacetyl]amino]-8-oxo-5-thia-1-azabicyclo[4.2.0]oct-2-ene-2-carboxylic acid sodium salt, one equivalent, and a molar equivalent of sodium bicarbonate are dissolved in a phosphate buffer, pH=6.4. A slight molar excess of 1-methyl-1H-tetrazol-5-ylthio is added and the solution is stirred for about 6 hours at 60° C. The pH is adjusted to about 3 by the addition of hydrochloric acid. Ethyl acetate is used to extract the product. The ethyl acetate solution is washed with saturated sodium chloride solution and dried over magnesium sulfate. Then the ethyl acetate is removed under vacuum below 50° C. and the title compound is recovered.

EXAMPLE 8

7-[[(1H-Indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid 3-[(Acetyloxy)methyl]-7-[[2-1H-indol-1-ylacetyl]amino]-8-oxo-5-thia-1-azabicyclo[4.2.0]oct-2-ene-2-carboxylic acid sodium salt, one equivalent, and a molar equivalent of sodium bicarbonate are dissolved in a phosphate buffer, pH=6.4. A slight molar excess of 5-methyl-1,3,4-thiadiazol-2-ylthio is added and the solution is stirred for about 6 hours at 60° C. The pH is adjusted to about 3 by the addition of hydrochloric acid. Ethyl acetate is used to extract the product. The ethyl acetate solution is washed with saturated sodium chloride solution, dried over magnesium sulfate. Then the ethyl acetate is removed under vacuum below 50° C. and the title compound is recovered.

EXAMPLE 9

3-[(Acetyloxy)methyl]-7-[[2-carboxy-2-(1H-indol-1-yl)acetyl]amino]-8-oxo-5-thia-1-azabicyclo[4.2.0]oct-2-ene-2-carboxylic acid, tert-butyl ester To a solution of 0.140 mole of 1H-indol-1-ylmalonic acid in 500 ml of dry ether is added 0.145 mole of thionyl chloride and 1 drop of dimethylformamide. This mixture is refluxed for 3 hours and the solvent and excess thionyl chloride is removed under a vacuum at room temperature. Dry benzene is added to the residue and the benzene is distilled to remove the last trace of thionyl chloride to give the monoacid chloride of 1H-indol-1-ylmalonic acid.

The monoacid chloride of 1H-indol-1-ylmalonic acid (0.1 mole) is dissolved in 300 ml of dry tetrahydrofuran and then added to 0.1 mole of 3-acetyloxymethyl-7-amino-8-oxo-5-thia-1-azabicyclo[4.2.0]oct-2-ene-2-carboxylic, tert-butyl ester in about 250 ml of water, 150 ml of ethyl ether and 0.1 mole of sodium hydroxide dissolved in 100 ml of water. The mixture is stirred for about 60 minutes, the pH adjusted to about 2 with addition of hydrochloric acid and the layers separated. The organic layer is dried, filtered and evaporated to give the title compound.

EXAMPLE 10

3-[(Acetyloxy)methyl]-7-[[2-carboxy-2-(1H-indol-1-yl)acetyl]amino]-8-oxo-5-thia-1-azabicyclo[4.2.0]oct-2-ene-2-carboxylic acid A solution of 3-[(acetyloxy)methyl]-7-[[2-carboxy-2-(1H-indol-1-yl)acetyl]amino]-8-oxo-5-thia-1-azabicyclo-[4.2.0]oct-2-ene-2-carboxylic acid, tert-butyl ester (0.05 mole) in 10 ml of trifluoroacetic acid maintained at 0° C. is stirred for 10 minutes. The trifluoroacetic acid is removed under vacuum. The residue is treated with ethyl ether to give a solid material. Filtration gives the title compound.

EXAMPLE 11

7-[[(1H-Indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid N-ethoxy-N-methyl aminomethyl ester The sodium salt of 3-[[(1H-indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid, 2.5 mmole, in 50 ml of dimethylformamide (DMF) is treated at room temperature with 2.5 mmole of N-chloromethyl-N-methylurethane for 1 hour. The mixture is carefully poured into ice water and the precipitated solid is removed by filtration and washed with water. The solid is dissolved in ethyl acetate and washed with aqueous sodium bicarbonate and then with water. The ethyl acetate is dried, filtered and evaporated to give the title compound.

EXAMPLE 12

7-[[2-Carbethoxy-2-(1H-indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid, 2-amino-3-methyl butyryloxymethyl ester A suspension of 5 grams of 7-[[2-carbethoxy-2-(1H-indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid sodium salt and 8.5 grams of N-tert-butoxycarbonyl-L-valine chloromethyl ester, prepared by the general procedure described in W. German Offen. No. 2,236,620 are mixed in 100 ml of dimethylformamide (DMF) and stirred for 72 hours. The mixture is diluted with ethyl acetate, washed with water, aqueous sodium bicarbonate and again with water. The ethyl acetate portion is dried over magnesium sulfate, filtered and evaporated to dryness to give 7-[[2--carbethoxy-2-(1H-indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid N-tert-butoxycarbonyl-2-amino-3-methylbutyryloxymethyl ester from which the protecting group can be removed by standard procedures to give the title compound.

EXAMPLE 13

7-[[(1H-Indol-1-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid pivaloyloxymethyl ester The sodium salt of 7-[[(1H-indol-1-ylacetyl)amino]-3-[[(5-methyl-1,3,4-thiadiazol-2-yl)thio]methyl-8-oxo-5-thia-1-azabicyclo[4.2.0]oct-2-ene-2-carboxylic (3 grams) was added to about 40 ml of dry dimethylformamide (DMF) and stirred for about 30 minutes. Then 4.0 ml of chloromethyl pivalate in 5 ml of DMF was added. The mixture was stirred for about 4 hours at room temperature. This mixture is diluted with ethyl acetate and thoroughly washed with water. The ethyl acetate portion is dried over sodium sulfate, filtered and evaporated to give the title compound.

EXAMPLE 14

7-[[(1H-Indol-1-yl)acetyl]amino]-3-methyl-8-oxo-5-thia-1-azabicyclo[4.2.0]oct-2-ene-2-carboxylic acid p-pivaloyloxybenzyl ester 7-[[(1H-Indol-1-yl)acetyl]amino]-3-methyl-8-oxo-5-thia-1-azabicyclo[4.2.0]oct-2-ene-2-carboxylic acid, sodium salt, 6.6 mole, is added to 35 ml of dimethylformamide (DMF) with stirring. Then 2 equivalents of pivaloyloxybenzyl alcohol is added and the mixture cooled to 0° C. To this is added 7.2 mmole of dicyclohexylcabodiimide in 7.5 ml of DMF. Stirring is continued at 0° C. for 1 hour and an additional 4 hours at room temperature. The dicyclohexyl urea which is formed is removed by filtration. The reaction mix is diluted with ethyl acetate, washed thoroughly with water and the ethyl acetate is dried and filtered. Evaporation of the ethyl acetate gives the title compound.

EXAMPLE 15

7-[[2-Carbethoxy-2-(1H-indol-1-yl)acetyl]amino]-3-methyl-8-oxo-5-thia-1-azabicyclo[4.2.0]oct-2-ene-2-carboxylic acid, tert-butyl ester The monoethyl ester of 1H-indol-1-ylmalonic acid (3.96 mmole), (3.96 mmole) of 7-amino-3-methyl-8-oxo-5-thia-1-azabicyclo[4.2.0]oct-2-ene-2-carboxylic acid, tert-butyl ester and (3.96 mmole) of N-ethoxycarbonyl-2-ethoxy-1,2-dihydroquinoline (EEDQ) are mixed in 50 ml of hydrocarbon stabilized chloroform. The mixture is stirred overnight at room temperature under a nitrogen atmosphere. The reaction mixture is diluted with chloroform, washed with dilute aqueous hydrochloric acid, dilute aqueous sodium bicarbonate and water. The chloroform solution is dried over magnesium sulfate, filtered and evaporated to dryness to give the title compound.

EXAMPLE 16

7-[[(1H-Indol-1-yl)acetyl]amino]-3-chloro-8-oxo-5-thia-1-azabicyclo[4.2.0]oct-2-ene-2-carboxylic acid (1H-Indol-1-yl)acetic acid (0.05 m) is added to tetrahydrofuran. The temperature is lowered to about −10° C. and 1 equivalent of isobutylchloroformate in tetrahydrofuran is added. This mixture is stirred for about 30 minutes. A solution of 7-amino-3-chloro-8-oxo-5-thia-1-azabicyclo[4.2.0]oct-2-ene-2-carboxylic acid in 1:1 tetrahydrofuran/water containing 1 equivalent of triethylamine is added to the previously formed solution maintained at −10° C. The resulting solution is stirred for about 60 minutes at −10° C. to 0° C. and then stirred for 60 minutes at 0° C. to 30° C. The solvents are removed at reduced pressure to give a residue which is extracted with ethyl acetate. The ethyl acetate is dried over magnesium sulfate, filtered and evaporated to give the title compound.

EXAMPLE 17

(1H-Indol-1-yl)malonic acid, monoacetyloxymethyl ester (1H-Indol-1-yl)malonic acid (0.30 mole) is added to dimethylformamide which contains 0.30 mole of sodium hydroxide. This mixture is stirred for about 1 hour during which time the monosodium salt of (1H-indol-1-yl)malonic acid is formed. The thus formed salt is then reacted with acetyloxymethyl chloride over a period of 60 minutes at room temperature. The mixture is poured into ice water and then extracted with ether. The ether extract is washed with water to remove the dimethylformamide. The ether is dried over magnesium sulfate, the magnesium sulfate is removed and on evaporation of the ether, the title compound is recovered.

We claim:

1. A compound selected from the formula

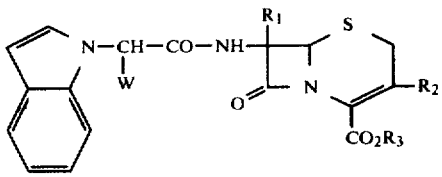

wherein W is hydrogen, a —$CO_2R_4$ group wherein $R_4$ is hydrogen, a straight or branched 1 to 4 carbon alkyl group, a straight or branched alkanoyloxymethyl group in which the alkanoyl group has from 2 to 5 carbon atoms; $R_1$ is hydrogen or methoxy; $R_2$ is chloro, bromo or methoxy, $R_3$ is hydrogen, a straight or branched alkyl group of from 1 to 4 carbon atoms, a straight or branched alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen is substituted with a straight or branched alkyl group having 1 to 4 carbon atoms or is unsubstituted; an alkoxycarbonylaminomethyl group in which the alkoxy moiety is straight or branched and has from 1 to 4 carbon atoms and the amine nitrogen is substituted with a straight or branched alkyl group of from 1 to 4 carbon atoms or is unsubstituted, p-(alkanoyloxy)benzyl group in which the alkanoyl moiety is straight or branched and has from 2 to 5 carbon atoms; an aminoalkanoyloxymethyl group in which the alkanoyl moiety has from 2 to 15 carbon atoms and the amino nitrogen is mono- or di-substituted with a straight or branched alkyl group having from 1 to 4 carbon atoms or is unsubstituted; or pharmaceutically acceptable salts thereof.

2. A compound according to claim 1 wherein $R_1$ is methoxy.

3. A compound according to claim 1 wherein $R_1$ is hydrogen.

4. A compound according to claim 3 wherein $R_3$ is hydrogen.

5. A compound according to claim 4 wherein W is hydrogen.

* * * * *